United States Patent
Arzt

[11] Patent Number: 5,509,804
[45] Date of Patent: Apr. 23, 1996

[54] BASE FOR DENTAL PROSTHESIS AND THE LIKE FOR IMPLANTATION IN BONE

[76] Inventor: Erich Arzt, Via della Mendola 46/19, I-39100 Bolzano, Italy

[21] Appl. No.: 290,906
[22] PCT Filed: Mar. 2, 1993
[86] PCT No.: PCT/EP93/00464
§ 371 Date: Aug. 23, 1994
§ 102(e) Date: Aug. 23, 1994
[87] PCT Pub. No.: WO93/17634
PCT Pub. Date: Sep. 16, 1993

[30] Foreign Application Priority Data

Mar. 4, 1992 [IT] Italy ................. T092A0179

[51] Int. Cl.$^6$ ........................... A61C 13/28
[52] U.S. Cl. ........................... 433/169; 433/173
[58] Field of Search ................. 433/169, 172, 433/173, 174, 175, 176

[56] References Cited

U.S. PATENT DOCUMENTS

| | | | |
|---|---|---|---|
| 4,881,897 | 11/1989 | Franek et al. | 433/169 |
| 5,033,962 | 7/1991 | Scatena | 433/169 |
| 5,040,982 | 8/1991 | Stefan-Doger | 433/169 |
| 5,425,639 | 6/1995 | Anders | 433/169 |

*Primary Examiner*—Christopher A. Bennett
*Attorney, Agent, or Firm*—Sughrue, Mion, Zinn, Macpeak & Seas

[57] ABSTRACT

The base for a dental prosthesis includes an outer body of biocompatible metallic material with a cavity in which an inner body of biocompatible metallic material with a seat for holding a prosthesis is disposed with the interposition of a layer of shock-absorbent material. An annular retaining element connected to the edge of the cavity in the outer body has a resiliently-deformable inner edge which engages a corresponding outer collar on the inner body so as to be resiliently preloaded thereby.

9 Claims, 2 Drawing Sheets

BASE FOR DENTAL PROSTHESIS AND THE LIKE FOR IMPLANTATION IN BONE

BACKGROUND OF THE INVENTION

The present invention relates to a base for dental prosthesis and the like for implantation in bone.

More specifically, the subject of the invention is a base for implantation in bone, including an outer body of rigid material, preferably a biocompatible metallic material, having means for anchoring it to the bony tissue and a cavity in which an inner body, also made of a rigid material, preferably a biocompatible metallic material, with a seat for holding a prosthesis is disposed with the interposition of a layer of resiliently shock-absorbent bonding material; an annular retaining element being connected to the edge of the cavity in the outer body and having an inner edge.

A base for implantation in bone of the type specified above is disclosed in WO-A-8 706 816 (FIG. 4).

In that prior implantation base the inner edge of the annular retaining ring merely overlies the upper portion of the resilient bonding material interposed between the outer body and the inner body. With this construction the resilient bonding material is not sealingly prevented from coming into contact with food and/or mouth fluids which can seep through the interspace between the retaining ring and the inner body and cause a degradation of said resilient bonding material.

Other bases for implantation in bone are described, for example, in U.S. Pat. No. 4 780 080, French patent application 2 580 169, and Dutch patent application 8200711.

The bases for implantation in bone described in these documents have the disadvantage that the resiliently shock-absorbent bonding material interposed between the inner and outer bodies extends to the top of the base and, in the condition of use, is in contact with the surrounding tissue, particularly the gum tissue. This material can thus come into contact with food and various liquids introduced into the mouth and may sooner or later become degraded.

SUMMARY OF THE INVENTION

The object of the present invention is to provide a base for implantation in bone which overcomes the problem of the bases of the prior art described above.

According to the invention, this object is achieved by means of a base for implantation in bone of the type specified above, characterized in that the inner edge of the annular retaining element is in engagement with a corresponding outer collar on the inner body so as to be resiliently preloaded thereagainst.

In the base for implantation in bone according to the invention, the retaining ring connected to the outer body prevents the inner body from coming out of the cavity in the outer body and, in particular, isolates the layer of shock-absorbent material interposed between them from the outside environment. By virtue of the resilient preloading of the edge of the retaining element, the shock-absorbent material is isolated even when the inner body performs very small movements inwardly of the cavity in the outer body, resiliently compressing the shock-absorbent material between the bodies, during chewing.

BRIEF DESCRIPTION OF THE DRAWINGS

Further characteristics and advantages of the invention will become clear from the detailed description which follows with reference to the appended drawings, provided purely by way of non-limiting example, in which.

DETAILED DESCRIPTION OF THE INVENTION

Figure 1:
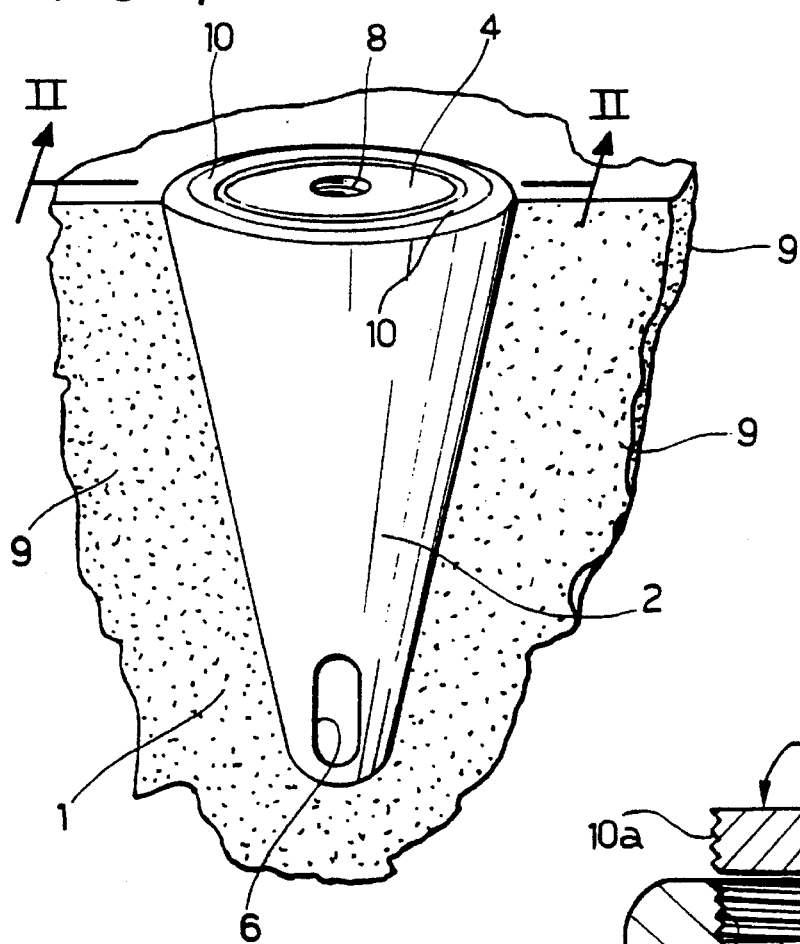
FIG. 1 is a perspective view of a base for dental prosthesis for implantation in bone according to the invention.

In the drawings, a base for implantation in bone according to the present invention is generally indicated 1.

The base has a monolithic structure including a substantially conical outer body 2 made of a rigid material, preferably a biocompatible metallic material such as titanium or an alloy thereof.

The outer body 2 has a cavity 3 (FIGS. 2 to 4) which is also substantially conical and in which an inner body 4, also made of a rigid material, preferably a biocompatible metallic material such as titanium or an alloy thereof, is disposed.

The inner body 4 extends within the outer body and a space, also substantially conical, defined between them is filled with a layer of electrically-insulating and resiliently shock-absorbent bonding material 5, for example, a polymeric material.

The bottom of the outer body 2 has at least one hole 6, in known manner.

The top of the inner body 4 has a seat for retaining and supporting a dental prosthesis and/or an accessory thereof. In the embodiment shown by way of example, the seat is constituted by a threaded hole, indicated 8 in FIGS. 1 and 2.

Figure 3:
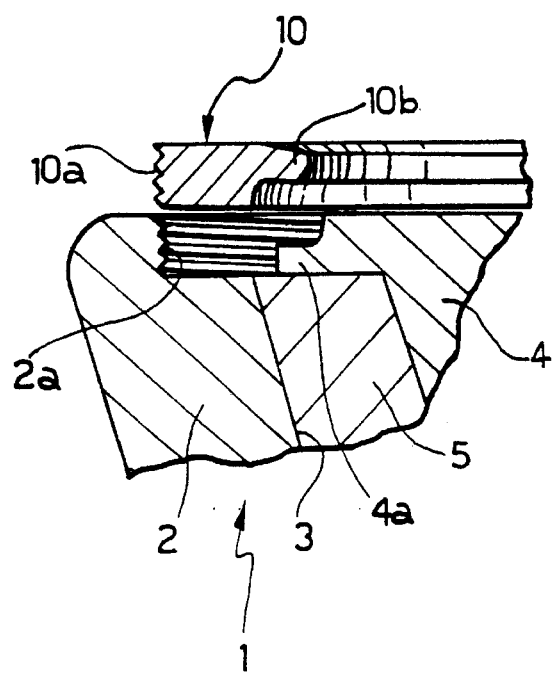
FIG. 3 is a partial section showing a detail of the base according to the invention during the fixing of the retaining ring to the outer body.
Figure 4:
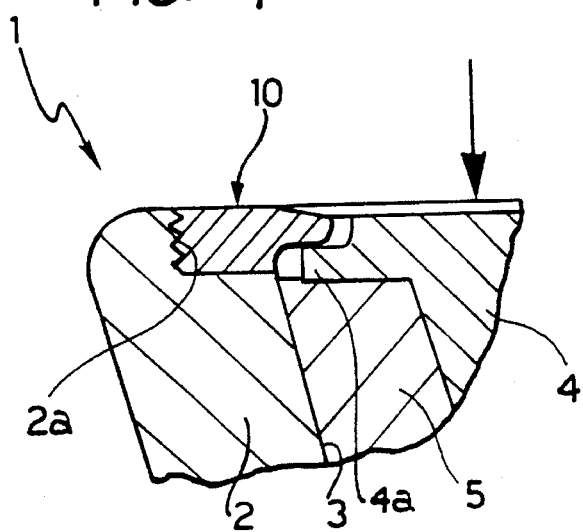
FIG. 4 is a view showing the same detail as FIG. 3 in a working condition.
Figure 2:
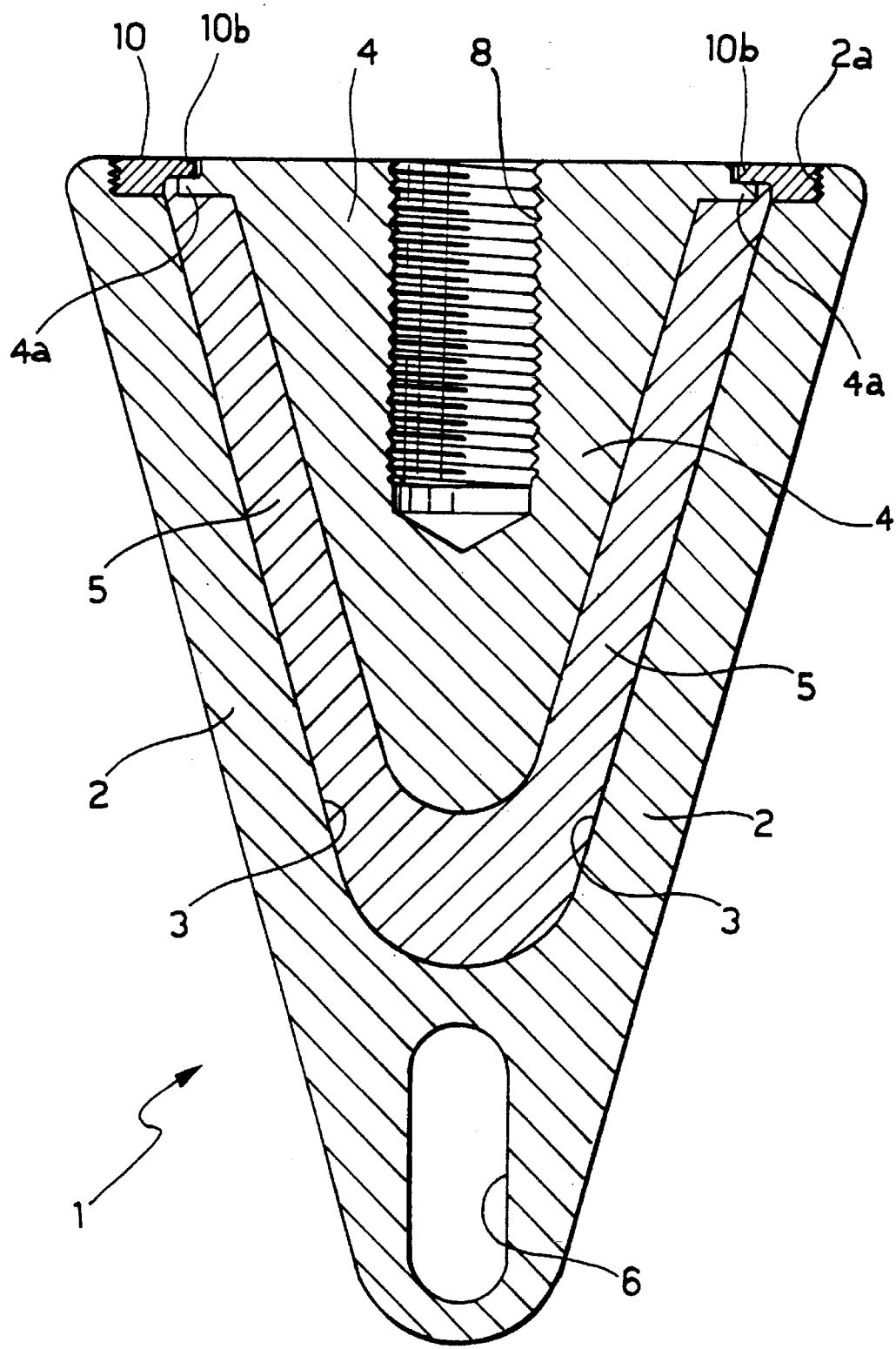
FIG. 2 is a section taken on the line II—II of FIG. 1.

The mouth of the cavity 3 in the outer body 2 has an internal threaded edge, indicated 2a in FIGS. 2 to 4.

The inner body 4 has an integral, outer collar, indicated 4a, at its upper end.

A retaining ring or ring nut, indicated 10, has an external thread 10a by means of which it can be screwed into the thread 2a of the outer body 2.

As can best be seen in FIG. 3, the retaining ring 10 has an inner edge 10b of reduced thickness so as to be resiliently deformable. In the embodiment shown by way of example, this edge is slightly funnel-shaped.

The radial width of the edge 10b of the retaining ring 10 is such that, when the ring is screwed into the thread 2a of the outer body 2, the edge 10b overlaps the outer collar 4a of the inner body.

Conveniently, according to the invention, the retaining ring 10 is formed so that, when it is screwed fully into the threaded seat 2a in the outer body 2, its inner edge 10b presses against the collar 4a of the inner body so as to be resiliently preloaded thereby, as shown in FIG. 2 in which the edge appears to be substantially flat.

The ring 10 not only prevents the inner body 4 from coming out of the outer body 2 but also completely isolates the layer 5 of shock-absorbent material between the bodies from the outside environment.

By virtue of the resilient preloading of the edge 10b against the outer collar of the inner body 4, the layer 5 is isolated even when the inner body 4 performs very small movements towards the bottom of the cavity 3 in the outer body 2 as a result of chewing, as shown in FIG. 4.

The retaining ring or ring nut 10 may also conveniently be made of a biocompatible metallic material, for example, titanium or an alloy thereof.

If the inner body 4 and the outer body 2 are to be electrically insulated from each other, the annular retaining element 10 may be made of an electrically-insulating material or of a metallic material with a surface layer of electrically-insulating material, at least on its surface which contacts the collar of the inner body 4.

Instead of or as well as this measure, the collar 4a of the inner body 4 may have a covering of electrically-insulating material in the region which contacts the retaining ring 10.

In use, the base 1 is positioned in a seat, indicated 9 in FIG. 1, of a substantially complementary shape in the bony tissue of the jaw. The hole 6 is intended to form a firm anchorage for the implant 1 as a result of the growth of bony tissue within it (osteointegration). When osteointegration has taken place, the hole 6 also prevents the base from rotating.

The cavity 3 in the outer body 2 and the outer surface of the inner body 4 may conveniently be formed so as to be of have elliptical cross-section in order to prevent the inner body 4 from rotating relative to the outer body 2.

Alternatively, at least one longitudinal portion of the cavity 3 in the outer body 2 and a corresponding longitudinal portion of the outer surface of the inner body 4 may be substantially pyramidal in shape.

Naturally, the principle of the invention remaining the same, the forms of embodiment and details of construction may be varied widely with respect to those described and illustrated purely by way of non-limiting example, without thereby departing from the scope of the present invention.

Thus, for example, the retaining ring or ring nut 10 may be fixed to the outer body 2 by a connection other than the threaded connection described above, for example, by gluing, cementing, upsetting, etc.

What is claimed is:

1. A base for a dental prosthesis for implantation in bone, including an outer body of rigid biocompatible metallic material having means for anchoring it to bony tissue and a cavity, an inner body of a rigid biocompatible metallic material having a seat for holding a prosthesis disposed in said cavity and a layer of resilient shock absorbent bonding material disposed between said outer body and said inner body;

an annular retaining element being connected to an edge of the cavity in the outer body and having an inner edge; wherein the inner edge of the annular retaining element is in engagement with a corresponding outer collar on the inner body so as to be resiliently preloaded against the inner body.

2. A base for implantation in bone according to claim 1, wherein the retaining element is constituted by a ring nut having an external thread for coupling with a corresponding thread near the edge of the cavity in the outer body.

3. A base for implantation in bone according to claim 1, wherein the inner edge of the annular retaining element is funnel-shaped.

4. A base for implantation in bone according to claim 1, wherein the annular retaining element is of a biocompatible metallic material.

5. A base for implantation in bone according to claim 4, wherein the annular retaining element has a layer of electrically-insulating material on its inner edge which is engagable with the collar of the inner body.

6. A base for implantation in bone according to claim 4, wherein the outer collar of the inner body has a surface layer of electrically-insulating material.

7. A base for implantation in bone according to claim 1, wherein the bonding material is a polymeric material.

8. A base for implantation in bone according to claim 1, wherein the cavity in the outer body and an outer surface of the inner body are of substantially elliptical cross-section.

9. A base for implantation in bone according to claim 1, wherein at least one longitudinal portion of the cavity in the outer body and at least one longitudinal portion of an outer surface of the inner body are substantially pyramidal in shape.

* * * * *